United States Patent [19]

Schreur

[11] 4,251,449
[45] Feb. 17, 1981

[54] METHOD OF MAKING A SOLID CRYSTALLINE COMPOSITION CONSISTING ESSENTIALLY OF CALCIUM ASCORBATE

[76] Inventor: Clarence Schreur, 14 Glenoaks, Prescott, Ariz. 86301

[21] Appl. No.: 9,480

[22] Filed: Feb. 5, 1979

Related U.S. Application Data

[63] Continuation-in-part of Ser. No. 595,234, Jul. 11, 1975, abandoned.

[51] Int. Cl.$^3$ .......................................... C07D 307/62
[52] U.S. Cl. .................................................. 260/343.7
[58] Field of Search ...................................... 260/343.7

[56] References Cited

U.S. PATENT DOCUMENTS

| | | | |
|---|---|---|---|
| 2,400,171 | 5/1946 | Ruskin | 260/343.7 |
| 2,442,005 | 5/1948 | Holland | 260/343.7 |
| 2,457,141 | 12/1948 | Freeman | 260/343.7 |
| 2,495,246 | 1/1950 | Fox et al. | 260/343.7 |
| 2,596,103 | 5/1952 | Ruskin | 260/343.7 |
| 2,631,155 | 3/1953 | Ruskin | 260/343.7 |

*Primary Examiner*—Norma S. Milestone
*Attorney, Agent, or Firm*—Sellers and Brace

[57] ABSTRACT

The invention is directed to a method of making crystalline calcium ascorbate by reacting ascorbic acid and calcium carbonate in liquid water medium, using some excess of carbonate, at a temperature of not more than about 70° C., under controlled conditions so that the reaction mixture is maintained saturated with carbon dioxide gas and a carbon dioxide foam blanket is maintained over the reaction mixture during the reaction time, said water being present in the reactor in an amount which provides a reaction product solution having a syrupy viscosity, and spontaneously crystallizing out of said syrup a mass consisting essentially of calcium ascorbate, which calcium ascorbate is a source of Vitamin C activity.

6 Claims, No Drawings

4,251,449

METHOD OF MAKING A SOLID CRYSTALLINE COMPOSITION CONSISTING ESSENTIALLY OF CALCIUM ASCORBATE

CROSS REFERENCE TO RELATED APPLICATION

This is a continuation-in-part application arising out of my copending application Ser. No. 595,234, filed July 11, 1975, now abandoned

BACKGROUND OF THE INVENTION

1. Field of the Invention

This invention relates to a composition having Vitamin C activity and to a method of making said composition. More particularly, the invention relates to the preparation of crystalline calcium ascorbate. Still more particularly, the invention relates to a method of making a crystalline mixture of calcium ascorbate and calcium ascorbate oxidizate.

2. Description of the Prior Art

Ruskin in U.S. Pat. No. 2,596,103, issued May 13, 1952, and in U.S. Pat. No. 2,631,155, issued Mar. 10, 1953, describes the preparation of crystalline calcium ascorbate dihydrate. (It is pointed that each of Ruskin's examples in each patent contains a common error, namely, 16.3 g of calcium carbonate is stated to equal ½ (0.5) mole of calcium carbonate. The molecular weight of calcium carbonate is 100.08. Therefore, Ruskin actually used 16.3 g/100.08 g=0.163 mole (1/6 mole) of calcium carbonate reactant in each of his examples in both patents) Ruskin used in each example in both patents 60 g of ascorbic acid reactant. The molecular weight of ascorbic acid is 176.05. So Ruskin used 60 g/176.05 g=0.342 mole of ascorbic acid. Therefore, Ruskin used a mole ratio of ascorbic acid/calcium carbonate of 0.342/0.163=2.10—the stochiometric amount is 2.0. Thus Ruskin used an excess of ascorbic acid in each of his exemplary procedures.

Ruskin prepares seed crystals of calcium ascorbate dihydrate by reacting, at room temperature, some excess of ascorbic acid in liquid water solution with calcium carbonate; after removing dissolved carbon dioxide gas from the reaction product solution, calcium ascorbate is precipitated from the aqueous solution by a water miscible organic solvent, such as, acetone, methyl alcohol, or ethyl alcohol; the organic solvent is separated to obtain a gummy solid; the gummy solid is dissolved in water; the water is evaporated to recover a crystalline mass of calcium ascorbate dihydrate. (Each of the Ruskin patents at Example 1.)

Ruskin prepares crystalline calcium ascorbate dihydrate in another procedure, as follows: An aqueous solution of calcium ascorbate is prepared by a reaction identical with that used in Example 1; then the aqueous solution is evaporated until a syrup solution is obtained. The syrup is seeded with a few crystals from the batch prepared in Example 1. The seeded syrup solidifies into a solid mass of crystals. The mother liquor is removed by filtering; the crystals are pressed to dryness; and the remaining liquid is removed by washing the crystals with absolute ethyl alcohol. The dry crystals are calcium ascorbate dihydrate. (Each of the Ruskin patents at Example 2.)

In another procedure, Ruskin prepares an aqueous solution of calcium ascorbate by the procedure of Example 1. To this aqueous solution, Ruskin adds a water miscibel organic solvent in an amount controlled to just avoid precipitation of any solid. Then the water-organic solvent solution of calcium ascorbate is seeded with crystals obtained in Example 1. The seeded solution forms prismatic crystals; these crystals were recovered by filtration of the crystal-solution dispersion. The recovered crystals were dried by washing with absolute alcohol; the dry crystals are calcium ascorbate dihydrate. (Each of the Ruskin patents at Example 3.)

SUMMARY OF THE INVENTION

It has been discovered that crystalline calcium ascorbate can be more easily prepared than by the Ruskin procedures:

The instant method uses a higher temperature in the reaction zone of not more than about 70° C., preferably between about 40° C. and about 60° C., preferably the reaction is begun at about ambient temperature and the temperature of the contents of the reaction zone is elevated (raised) as the reaction proceeds, reaching the final temperature more or less simultaneously with the termination of the reaction, as evidenced by the subsiding of the foam blanket over the contents of the reactor.

The instant method uses some excess of calcium carbonate reactant over the stochiometric requirement of one (1.00) mole of calcium carbonate for two (2.0) moles of ascorbic acid; desirably the mole ratio of calcium carbonate to ascorbic acid is between about 1.02/2.0 and about 1.15/2.0.

The instant method uses liquid water as the reaction medium. Preferably the ascorbic acid reactant and the water are first intermingled (mixed) in the reaction zone (reactor) and then the calcium carbonate is added incrementally thereto, substantially over the reaction time. Incrementally includes small discrete quantities of calcium carbonate or continuous addition of a stream of calcium carbonate—over the reaction time. The rate of addition of calcium carbonate is controlled to aid in maintaining carbon dioxide saturation and foam blanketing of the reaction zone contents.

The liquid water is present in the reaction zone at the start of the reaction in an amount such that the water solution of reaction product, consisting essentially of calcium ascorbate, has a viscosity of syrup, desirably a light syrup. Preferably the water is present at the beginning of the ascorbic acid-calcium carbonate reaction in an amount between about 25% and about 50% of the theoretical ascorbic acid solution water requirement at about 60° C. solution temperature. Preferably the syrupy solution contains between about 50% and 75% of dissolved calcium ascorbate reaction product, that is, 50–75 weight parts per 100 weight parts of water present.

The liquid contents of the reaction zone are maintained in a carbon dioxide gas saturated condition and blanketed with carbon dioxide gas foam by carbon dioxide produced as a reaction sideproduct, which saturation and blanketing is maintained over the duration of the reaction. The reaction terminates itself (ends) with the consumption of the ascorbic acid reactant; the termination point is evidenced by the subsiding of the carbon dioxide foam blanket over the reaction zone contents.

The syrupy reaction product solution consisting essentially of calcium ascorbate can be stored under conditions which decrease, slow down, decomposition of the ascorbate, and can be used as a source of Vitamin C active material. Calcium ascorbate has a Vitamin C activity substantially the same as ascorbic acid, which is Vitamin C itself.

It is preferred to recover the reaction product from solution in the syrup. The syrupy solution spontaneously (that is, no seeding is necessary) forms a crystalline mass consisting essentially of calcium ascorbate, upon cooling of the syrup. Calcium ascorbate is temperature sensitive and residual water (mother liquor) is removed from the crystalline mass at a temperature controlled to avoid any substantial decomposition of the calcium ascorbate. When the residual water is removed by evaporation, the temperature is controlled not to rise above about 65° C., preferably not more than 60° C. Other procedures are available for removing residual water, for example several are shown in the Ruskin patents.

The analysis of the reaction product crystalline mass is affected by the process conditions, especially the temperature to which the crystalline mass is exposed and by exposure to atmospheric oxygen. It has been observed that, typically the reaction product consists of about 85% calcium ascorbate, about 12–14% of calcium ascorbate oxidizate, and the remainder essentially excess (unreacted) calcium carbonate.

DESCRIPTION OF A PARTICULAR EMBODIMENT

EXAMPLE

In this example of the instant invention, the reactor was an open vessel provided with an agitator, thermometer and heater. A closed vessel such as an autoclave may be used.

250 parts (all parts herein are by weight) of distilled water was charged to the reactor at room temperature, about 25° C. (77° F.).

Then 352 parts (2.0 moles) of USP grade ascorbic acid was charged to the reactor.

Merck Index, 8th (1968) at page 105 gives the following solubility data for ascorbic acid in water: 25° C., 100 g in 300 g of water or 33% solubility; 40% at 45° C., and 80% at 100° C. Plotting these values gives a chart readout of approximately 50% solubility at 60° C. The 250 parts of water charged in this example has a theoretical ascorbic acid solution capability at 60° C. of 125 parts of ascorbic acid. The 352 parts of ascorbic acid charged result in a % theoretical ascorbic acid solution water requirement at about 60° C. of $(125/352)(100)=36\%$. Desirably, the % theoretical ascorbic acid solution water requirement at about 60° C. falls in the range between about 25% and about 50%.

The water and ascorbic acid were mixed while incremental portions of finely divided calcium carbonate were added to the reactor. The reaction of the acid and the carbonate produced carbon dioxide gas. The agitation was controlled during the reaction along with the calcium carbonate addition rate to maintain a carbon dioxide foam blanket cover over the contents of the reactor —this also maintains a carbon dioxide gas saturated condition of the liquid content of the reactor.

The temperature of the reaction mixture was elevated (raised) as the incremental addition of the calcium carbonate was continued. The two rates: raising the temperature to a final temperature of 60° C. and adding the calcium carbonate were controlled to introduce all the carbonate by the time the temperature reached 60° C. The total amount of the calcium carbonate added was 105 parts (1.05 moles) to provide a mole ratio of carbonate charged/acid charged of 1.05/2.0.

Because the reactor in this example was open topped, another element entered into control of the reaction rate. The effervescence of carbon dioxide gas was maintained as rapidly as possible without the foam flowing out the top of the reactor.

Consumption of the ascorbic acid, which is present in less than the stochiometric amount of 1.00/2.0, causes the reaction to terminate itself (that is, stop), which termination is evidenced by subsiding of the foam blanketing of the reactor contents.

The liquid solution of reaction product in the reactor had a thin syrupy viscosity. This syrup can be stored in closed containers and used as a Vitamin C material. Calcium ascorbate has a Vitamin C activity substantially equally to ascorbic acid (Vitamin C itself).

Without removal of any of the carbon dioxide still dissolved in the syrup solution of reaction products, the syrup was poured from the reactor into trays. Desirably, the syrup contains 50%–75% of dissolved calcium ascorbate and associated other reaction product.

In the trays, the syrup, as it cooled, spontaneously (that is, no seeding with calcium ascorbate crystals was necessary) formed into a solid crystalline mass of calcium ascorbate and other reaction product. It was observed that the size of individual crystals varied with the rate of cooling of the solution in the tray. Crystal size usually begins at about 0.25 mm diameter; the later formed crystals are noticeably larger in size, that is as the tray temperature approaches ambient room temperature.

The residual liquid (mother liquor) was evaporated from the crystalline mass at a temperature held below about 60° C.

The crystalline reaction product had a light tan color; was about 98% soluble in water at room temperature; was insoluble in acetone or ethyl alcohol; had a very slight, pleasant odor similiar to fresh baked bread; was practically tasteless; and a water solution had a neutral pH.

Analysis of the reaction product indicated an absence of salt of dehydroascorbic acid, which material can be obtained by oxidizing ascorbic acid. Calcium ascorbate is present in an amount of $85\pm2\%$. Unreacted calcium carbonate is present in an amount of about 2%. The remaining 12–14% is calcium ascorbateoxidizate which has not been positively identified but is believed to be, most probably, calcium bis dihyroxyascorbate.

It has been observed that the oxidized portion of the reaction product is active for the mitigation of the pain caused by arthritis, phlebitis, and gout. The calcium ascorbate-"active" calcium ascorbate oxidizate mixture produced by the example herein is also as effective when the treatment dosage is adjusted for the calcium ascorbate content. 400 milligrams of total reaction product taken three times a day have provided remarkable mitigation of the pain of aforesaid maladies. It is indicated that the oxidizate is calcium bis dihydroxyascorbate or a closely similar compound. It is also understood that other metal ions can be used to produce ascorbate products effective in mitigating pain of aforesaid maladies; however, calcium is the preferred metal ion. The calcium ascorbate- oxidizate reaction product can be pushed to an equilibrium composition of about 80% calcium ascorbate and about 20% oxidizate (and including unreacted calcium carbonate) by operation between about 65° C. and about 93° C. (150–200° F.), and optimally between about 76° C. and about 82° C. (170-180° F.). Reaction times for preparing the syrupy solution at these higher temperatures run about 4-8 hours.

Thus having described the invention, what is claimed is:

1. A method of preparing calcium ascorbate which method comprises:

reacting ascorbic acid and calcium carbonate at a temperature of about 40°-60° C. in the presence of liquid water, said water being present, at the start of the reaction, in an amount of about 25% and about 50% of the theoretical ascorbic acid solution requirement at about 60° C., while maintaining said reaction zone saturated with carbon dioxide, produced as a reaction side-product, and a layer of carbon dioxide foam blanketing said reaction zone, said ascorbic acid and said water first being intermingled in the reaction zone and then said calcium carbonate being added incrementally to said reaction zone substantially over said reaction time, the mole ratio of said calcium carbonate reactant to said ascorbic acid reactant being between about 1.02/2 and about 1.15/2 where thestochiometric ratio is 1.00/2, to obtain, when the reaction has terminated itself as evidenced by subsiding of said foam, a syrupy reaction product solution, which product consists essentially of calcium ascorbate and said syrupy solution contains between about 50% and about 75% of dissolved calcium ascorbate.

2. The method of claim 1 wherein when said reaction has terminated itself, separating from the syrupy reaction product solution, a crystalline mass consisting essentially of calcium ascorbate.

3. The method of claim 2 wherein residual water is removed from said crystalline mass at a temperature controlled to avoid any substantial amount of decomposition of said calcium ascorbate.

4. The method of claim 3 wherein said residual water is evaporated from said crystalline mass at a temperature of not more than about 65° C.

5. The method of claim 1 wherein said reaction is begun at about ambient temperature and the temperature of said reaction zone is elevated as the reaction proceeds, reaching a final temperature of about 60° C. when the reaction has terminated itself as evidenced by subsiding of said foam.

6. A method of preparing a crystalline composition consisting essentially of calcium ascorbate, which method comprises:
   a. 2.0 moles (352 parts by weight) of ascorbic acid are mixed together with 250 parts by weight of water, at about 25° C., in a reactor;
   b. 1.05 moles (105 parts by weight) of finely divided calcium carbonate are added to said reactor, while mixing is continued and said reactor contents are heated to about 60° C., all of said carbonate is added more or less simultaneously with the reactor contents attaining said 60° C.;
   c. the addition of calcium carbonate is controlled to provide effervesence of carbon dioxide reaction side-product saturating the reactor contents and blanketing said contents with carbon dioxide foam;
   d. maintaining said saturation and blanketing until the calcium carbonate and ascorbic acid reaction is terminated by itself as evidenced by the subsiding of said foam;
   e. the reactor contains a syrupy solution consisting essentially of calcium ascorbate and excess carbonate;
   f. the syrupy solution is poured into trays where spontaneous crystallization takes place; and
   g. the crystalline mass is heated at a temperature of not more than 60° C. to evaporate residual water, to obtain a dry crystalline mass consisting essentially of calcium ascorbate.

* * * * *